US007794967B2

(12) United States Patent
Virtanen et al.

(10) Patent No.: US 7,794,967 B2
(45) Date of Patent: Sep. 14, 2010

(54) METHOD AND KIT FOR DETECTION OF NOVEL PATHOGEN INHIBITORS

(75) Inventors: Anders Virtanen, Uppsala (SE); Leif Kirsebom, Uppsala (SE)

(73) Assignee: Bioimics AB, Uppsala (SE)

( * ) Notice: Subject to any disclaimer, the term of this patent is extended or adjusted under 35 U.S.C. 154(b) by 919 days.

(21) Appl. No.: 10/495,617

(22) PCT Filed: Nov. 21, 2002

(86) PCT No.: PCT/SE02/02116

§ 371 (c)(1),
(2), (4) Date: Oct. 28, 2004

(87) PCT Pub. No.: WO03/044230

PCT Pub. Date: May 30, 2003

(65) Prior Publication Data

US 2005/0118587 A1 Jun. 2, 2005

(30) Foreign Application Priority Data

Nov. 21, 2001 (SE) .................................. 0103876

(51) Int. Cl.
*G01N 33/53* (2006.01)
*G01N 33/566* (2006.01)
*A61K 49/00* (2006.01)
*C12Q 1/68* (2006.01)
*C07H 21/04* (2006.01)

(52) U.S. Cl. .............................. 435/32; 424/7.2; 435/6; 435/91.1; 435/91.31; 435/455; 436/501; 536/23.1; 536/23.7; 536/24.5

(58) Field of Classification Search .................... 435/6, 435/32, 91.1, 91.31, 455; 424/9.2; 436/501; 536/23.1, 23.7, 24.5
See application file for complete search history.

(56) References Cited

U.S. PATENT DOCUMENTS 5,679,548 A * 10/1997 Barbas et al. ............... 435/69.6
6,306,602 B1 * 10/2001 Sillekens et al. ................ 435/6

FOREIGN PATENT DOCUMENTS

WO WO 95/22114 1/1995
WO WO 01/40518 6/2001

OTHER PUBLICATIONS

Scherer et al., Approaches for the sequence-specific knockdown of mRNA, 2003, Nat. Biotechnol., 21(12), pp. 1457-1465.*
Mikkelsen, N. E. et al., Proc. Natl. Acad. Sci., vol. 96, pp. 6155-6160 (1999).*
Tekos, A. et al., FEBS Letter, vol. 485, pp. 71-75 (2000).*
Kufel, J. et al., RNA, vol. 4, pp. 777-788 (1998).*
Altman et al., "Ribonuclease P", *The RNA World*, Second Edition, 1999 Cold Spring Harbor Laboratory Press 0-87969-561-7/99.

J. Åström et al., "In vitro deadenylation of mammalian mRNA by a HeLA cell 3' exonuclease", *The EMBO Journal*, Oxford University Press, vol. 10 No. 10 pp. 3067-3071, 1991.
Jonas Åström et al., "Properties of a HeLa Cell 3' Exonuclease Specific for Degrading Poly (A) Tails of Mammalian mRNA*", *The Journal of Biological Chemistry*, 1992, The American Society for Biochemistry and Molecular Biology, Inc., vol. 267, No. 25, Issue of Sep. 5, pp. 18154-18159, 1992.
R.S. Brown et al., "Crystallographic and Biochemical Investigation of the Lead(II)-Catalyzed Hydrolysis of Yeast Phenylalanine tRNA", *Biochemstry*, 1985 American Chemical Society, 24, 4785-4801.
Bryan T. Eger et al., "Minimal Kinetic Mechanism for Misincorporation by DNA Polymerase I (Klenow Fragment)", *Biochemistry*, 1992 American Chemical Society, 31, 9227-9236.
Cecilia Guerrier-Takada et al., "The RNA Moiety of Ribonuclease P is the Catalytic Subunit of the Enzyme", *Cell*, vol. 35, 849-857, Dec. 1983 (Part 2).
Thomas Hermann et al., Aminoglycoside Binding to the Hammerhead Ribozyme: A General Model for the Interaction of Cationic Antibiotics wth RNA, *J. Mol. Biol.*, 1998 Academic Press Limited, 276, 903-912.
Leif A. Kirsebom et al., "Base pairing between *Escherichia coli* RNase P RNA and its substrate", *The EMBO Journal*, Oxford University Press, vol. 13 no. 20 pp. 4870-4876, 1994.
Leif A. Kirsebom et al., "Inhibition of RNase P Processing", *RNA-Binding Antibiotics*, Landes Bioscience, Georgetown, Texas, USA, 2001 Eurekah.com.
Joanna Kufel et al., "The P15-loop of *Escherichia coli* RNase P RNA is an autonomous divalent metal ion binding domain", *RNA*, 1998, 4:777-788, Cambridge University Press.
Gavin MacBeath et al., "Printing Proteins as Microarrays for High-Throughput Function Determination", *Science*, Sep. 8, 2000, vol. 289.
Javier Martínez et al., "A 54-kDA Fragment of the Poly(A)-specific Ribonuclease Is an Oligomeric, Processive, and Cap-interacting Poly(A)-specific 3' Exonuclease", *The Journal of Biological Chemistry*, The American Society for Biochemistry and Molecular Biology, Inc., vol. 275, No. 31, Issue of Aug. 4, pp. 24222-24230, 2000.
Nils E. Mikkelsen et al., "Inhibition of RNase P RNA cleavage by aminoglycosides", *Proc. Natl. Acad. Sci.*, vol. 96, pp. 6155-6160, May 1999 Biochemistry.

(Continued)

*Primary Examiner*—Jane Zara
(74) *Attorney, Agent, or Firm*—Porter Wright Morris & Arthur LLP

(57) ABSTRACT

The present invention relates to a method for detection of novel pathogen inhibitors using models of pathogen specific, and metal binding structures/domains representing essential cellular molecules. The method enables identification of inhibitors that bind to any specific RNA molecule or protein that are essential for cell growth, proliferation and differentiation. The invention also relates to a kit for use in the method. Furthermore, the invention relates to use of aminoglycosides in the development of new drugs.

13 Claims, 6 Drawing Sheets

OTHER PUBLICATIONS

Nils E. Mikkelsen et al., "Aminoglycoside binding displaces a divalent metal ion in a tRNA-neomycin B complex", *Nature Structural Biology*, vol. 8, No. 6, Jun. 2001.

Thomas a. Steitz, "DNA Polymerases: Structural Diversity and Common Mechanisms", *The Journal of Biological Chemistry*, vol. 274, No. 25, Issue of Jun. 18, pp. 17395-17398, 1999.

Thomas A. Steitz et al., "A general two-metal-ion mechanism for catalytic RNA", *Proc. Natl. Acad. Sci.*, vol. 90, pp. 6498-6502, Jul. 1993 Biochemistry.

Frank Walter et al., "Aminoglycoside-RNA interactions".

Staffan G. Svärd et al., "Phylogenetic comparative mutational analysis of the base-pairing between RNase P RNA and its substrate", *RNA*, (1996), 2:463-472, Cambridge University Press.

Sarah R. Kirk et al., "2-Aminopurine as a Real-time Probe of Enzymatic Cleavage and Inhibition of Hammerhead Ribozymes", *Bioorganic & Medicinal Chemistry*, 9, (2001), 2295-2301, Elsevier Science Ltd.

James A. Murray et al., "Antibiotic interactions with the hammerhead ribozyme: tetracyclines as a new class of hammerhead inhibitor", *Biochem. J.*, (1996), 317, 855-860, Department of Biology, Level 10, University of Leeds.

Apostolos Tekos et al., "Inhibition of eukaryotic ribonuclease P activity by aminoglycosides: kinetic studies", *Federal of European Biochemical Societies*, FEBS Letters 485 (2000) 71-75.

Stefan et al "McRNA: a database of metal ion binding sites in RNA structures," *Nucleic Acids Research*, 34:D131-D134 (2006).

Kirsebom, Biochime, 89(10):1183-94 (2007).

Egea et al, Current Opinion in Structural Biology, 15:213-220 (2005).

Moore et al, Annu. Rev. Biochem., 76:101-24 (2007).

\* cited by examiner

Escherichia coli

Mycoplasma hyopneumoniae

Helicobacter pylori

Mycobacterium tuberculosis

Chlamydia trachomatis

Simkania negevensis

P15-loop model RNA

METHOD AND KIT FOR DETECTION OF NOVEL PATHOGEN INHIBITORS

RELATED APPLICATION

This application is a 371 of PCT/SE02/02116 filed Nov. 21, 2002.

FIELD OF THE INVENTION

The present invention is within the field of molecular biology. More closely, the invention relates to a method and a kit for detection of novel pathogen inhibitors using models of pathogen specific, and metal binding RNA structures/domains representing essential cellular RNA molecules. The method enables identification of inhibitors that bind to any specific RNA molecule or protein that are essential for cell growth, proliferation and differentiation. Furthermore, the invention relates to use of aminoglycosides as starting compounds for drug development.

BACKGROUND OF THE INVENTION

RNA molecules are essential components of the cell and its primary structure dictates its folding. The function of the RNA is subsequently dictated by its structure. The overall structure of RNA molecules consists of small structural regions/domains that together build up the RNA structure. Consequently, small stable RNA structural regions/domains can be identified and be produced separately with a retained conformation as exemplified by Kufel and Kirsebom, 1998.

RNase P is a ribonucleoprotein complex present in all living cells (Altman and Kirsebom, 1999). It catalyses the removal of 5' leader sequences from tRNA precursors and similar molecules. In bacteria, RNase P consists of one RNA subunit and a small basic protein, and it has been shown that the catalytic activity is associated with its RNA subunit. The RNA alone derived from bacteria is able to cleave a number of substrates correctly and efficiently in vitro in the absence of the protein (Guerrier-Takada et al., 1983). The reaction catalyzed by RNase P RNA alone as well as in the presence of the RNase P protein requires divalent metal ions such as Mg2+. It has been proposed that cleavage proceeds through a trigonal bipyramidal transition state (SN2), where two Mg2+ ions participate in the chemistry of the cleavage (Warnecke et al., 1996) defined as the two metal ion cleavage mechanism. In addition, Mg2+ ions are important for correct folding of RNase P RNA and for the interaction between RNase P and its substrate (Altman and Kirsebom, 1999).

The two metal ions cleavage mechanism is considered to be a general mechanism of catalysis in breakage and formation of phosphodiester bonds. Besides its importance in catalyzing RNA mediated cleavage of phosphodiester bonds it is well known that it is used by protein enzyme for the same purpose. The polymerizing and exonucleolytic activities of *E. coli* DNA polymerase I are the paradigm for two metal ion mediated catalysis (Steitz and Steitz, 1993). Other protein enzymatic activities proceeding through the two metal ion catalysis mechanism: a variety of prokaryotic and eukaryotic DNA polymerases, RNA polymerases, deoxyribo- and ribonucleases, phosphatases, kinases etc.

Several aminoglycosides are known to interact with RNA and interfere with its function. For example neomycin B interferes with protein biosynthesis due to binding to ribosomal RNA, inhibits the activity of several RNA based biocatalysts (known ribozymes) including RNase P RNA (Walter et al., 1999; Mikkelsen et al., 1999). The inhibitory effect caused by neomycin has been suggested to be due to displacement of essential divalent metal ions (Herrman and Westhof, J. Mol. Biol. vol. 276, 903-912, 1998). Direct evidence for displacement of a divalent metal has been obtained (Mikkelsen et al., 2001).

SUMMARY OF THE INVENTION

The present inventors have now found that aminoglycosides are also are potent inhibitors of enzymes that depend on metal ions for their catalytic activity. The present inventors have used *Escherichia coli* Klenow polymerase (pol) and mammalian poly(A)-specific ribonuclease (PARN) as model enzymes. The inhibitory potential of several aminoglycosides have been tested and neomycin B has been found to be a potent inhibitor (Table 1). The neomycin B inhibition is pH dependent, suggesting that the nature of the interaction is electrostatic. Enzyme kinetic analyses show that neomycin B behave as a mixed non-competitive inhibitor. Iron mediated hydroxyl radical cleavage was used to locate functionally important metal ions of both enzymes and to establish that neomycin B interfered with iron mediated cleavage at the active sites of Klenow pol and PARN. The present inventors have found a mechanism of inhibition where the aminoglycoside binds in the active site of the enzyme and thereby displaces catalytically important divalent metal ions in analogy with the inhibition of RNA activity by aminoglycosides. Thus, the present inventors have found that aminoglycosides are potent inhibitors of enzymes depending on metal ions for their catalytic activity and as such they can be used to probe metal ion binding sites on enzymes.

TABLE 1

Inhibition effects of aminoglycosides on PARN and Klenow pol

| Aminoglycoside | appK$_i$(μM) (for PARN) | appK$_i$(mM) (for KL pol) |
| --- | --- | --- |
| Neomycin B | 0.4 ± 0.1 | 4.8 ± 0.3 |
| Paromomycin | 17.3 ± 3.5 | 10.3 ± 0.8 |
| Lividomycin | 18.7 ± 2.8 | 11.6 ± 2.0 |
| Kanamycin B | 7.3 ± 0.4 | 9.2 ± 0.3 |
| Kanamycin A | 64.7 ± 7.8 | 14.3 ± 1.7 |
| Tobramycin | 7.1 ± 0.2 | 9.3 ± 0.7 |

We have previously suggested that aminoglycosides can be considered as "metal mimics" (Mikkelsen et al. 2001), since they bind to metal ion binding sites of RNA molecules and interfere with the function of RNA by displacing functionally/structurally important divalent metal ions. The present inventors have now established that aminoglycosides also interfere with metal ion binding sites of protein enzymes, showing that the "metal mimics" property of aminoglycosides is not only restricted to the interaction between aminoglycosides and RNA. Thus, aminoglycosides as "metal mimics" can be used as functional probes to perturb the catalytic activity of both ribozymes and metalloenzymes, and as functional/structural probes to map and characterize the active sites of such catalytic activities. We expect that aminoglycosides as "metal mimics" can serve as starting compounds for development of novel drugs (e.g. antibiotics) and that aminoglycosides or derivatives thereof can be used as ligands to identify metal binding proteins in systematic screening efforts using the protein microarray technique recently developed by MacBeath and Schreiber (MacBeath and Schreiber 2000).

The present invention relates to a method for identification of novel antibiotics/lead compounds directed against microorganisms including viruses. The method is particularly suitable for selecting novel antibiotics/lead compounds with high specificity for target molecules/microorganism and with low toxicity i.e. with few side effects on the treated patient/host. The strategy/method of the invention relies on targeting the novel antibiotic/lead compound against RNA or protein molecules that are essential for growth, proliferation and/or differentiation of the selected microorganism. The selected RNA or protein molecules should be metal binding and show distinct structural differences compared to its eukaryotic counterpart or be absent in the treated host.

The present invention provides an improved way of selecting novel antibiotics interacting with a specific target (RNA and/or protein) and limits unwanted side effects. Furthermore, the invention includes a differential screening procedure to identify toxic side effects of selected compounds wherein specific protein enzymes that depend on metal ions for activity are used. A major advantage is therefore that this strategy/method minimises the usage of animal experimental model systems.

The inventive strategy/method may in principle be used to identify any compound that confers their inhibitory activity by displacing divalent metal ions, for example to identify novel metal mimics. Hence, the invention can also be used to select and screen for inhibitors of protein enzymes that depend on divalent metal ions for activity and reducing toxic side effects. Examples can be inhibition of essential enzymes encoded by pathogenic/tumor viruses and pathogenic microorganisms. According to the invention, the term pathogens is intended to include animal pathogens, plant pathogens and human pathogens. The pathogens may be procaryotic or eucaryotic or their viruses.

Exemplifying Strategy

1. Specific regions/domains of RNase P RNA unique to, for example, bacterial RNase P RNA is chosen. These regions/domains are produced as small model RNA molecules and used to select for compounds that specifically binds to these regions/domains.

2. Selected compounds are tested for inhibitory activity in vitro using RNase P RNA alone and RNase P RNA in the presence of the RNase P protein (in bacteria referred to as the C5 protein). Those inhibitory compounds are selected which do not affect eukaryotic RNase P activity.

3. The selected compounds are tested for inhibition of various protein enzyme activities that depend on metal ions for activity.

4. The compounds that fulfil the criteria to inhibit bacterial RNase P activity specifically will subsequently be tested in bacteria infected cell cultures. The criteria will be that bacterial growth should be inhibited specifically.

5. Optionally, step 4 is repeated in animal models.

In a first aspect, the invention relates to a method for detection of novel pathogen inhibitors, characterised by the following steps:

a) providing a model molecule (which may be RNA or protein and may be chemically or recombinantly produced and which also comprise chemically or enzymatically modified and mutated variants thereof) comprising at least one functionally important, pathogen unique and metal binding region/domain of an essential cellular macromolecule, wherein pathogen unique means derived from pathogen microorganisms and virus of any source; and
b) screening for compounds interacting/binding to said model molecule. The binding may be detected spectrophotometrically, by surface plasmon resonance, by gel electrophoresis or by chromatographic methods (for proteins).

Optionally the method comprises
c) testing said compounds for inhibition of human metal dependent (house keeping) enzymes, and selecting compounds which do not inhibit said enzymes. This step is very valuable for diminishing side effects of the pathogen inhibitor in the treated patient.

Further optional steps in the method are:
d) testing said compounds for inhibition of corresponding full size pathogenic RNA molecule both alone and in the presence of its corresponding protein and selecting compounds with inhibiting properties, wherein strong or weak inhibiting properties may be desired; and
e) cultivation of corresponding pathogen in the presence of inhibitor, wherein bacterial growth is to be substantially inhibited.

The model molecule provided in step a) is RNA or protein.

In a preferred embodiment the model molecule provided in step a) is linked to a solid support, such as a strip or beads, for example biotionylated RNA binding to streptavidine beads.

Step b) may be by detection of RNA or protein cleavage in vitro, wherein interaction/binding of inhibiting compounds prevents RNA/protein cleavage.

The possible cleavage may, for example, be detected electrophoretically using radioactive or fluorescent labelling.

Preferably the RNA/protein cleavage is induced by $Pb^{2+}$ or $Fe^{2+}$-mediated hydroxyl radical cleavage.

Alternatively, step b) is by detection of bacterial growth in vivo, wherein the following bacteria are cultivated in the presence of a suspected inhibitor:
i) bacteria transformed with a plasmid not encoding any model RNA/protein or untransformed bacteria
ii) bacteria transformed with a vector comprising a gene encoding the model RNA molecule according to step a) and a self cleaving RNA structure element;
wherein inhibition of growth in step i) and cell growth in step ii) indicates the presence of an inhibitor.

This may also be used to test an in vitro identified inhibitor.

In a second aspect, the invention relates to a kit for detection of novel pathogen inhibitors, characterised in
i) metal binding and pathogen unique model molecules for use in step a) of the above method; and optionally
ii) one or more human metal dependent enzymes for use in step c) of the above method; and optionally
iii) $Pb^{2+}$ for use in step b) of the above method.

The model molecules may be provided as synthetically produced molecules.

Alternatively, the model molecules are provided in vectors carrying genes encoding said model molecules harbouring sequences encoding functionally important domains of essential cellular RNA molecules which are autonomous divalent metal ion binding sites for recombinant production of the model molecules.

The model molecules are derived from RNA or protein.

In a preferred embodiment the model RNA gene sequences encode P15, P15/P16-loop, P16 or P17 of RNase P RNA of bacterial origin, such as from *Mycobacterium tuberculosis*.

In a third aspect, the invention relates to use of aminoglycosides as starting compounds for drug development.

In a fourth aspect, the invention relates to use of aminoglycosides for production of a drug for inhibition of pathogenic meta 110 enzymes, i.e. for treatment of pathogenic conditions involving such enzymes.

IN VITRO METHOD

A Structural Differences of Target RNA

Figure 1A:
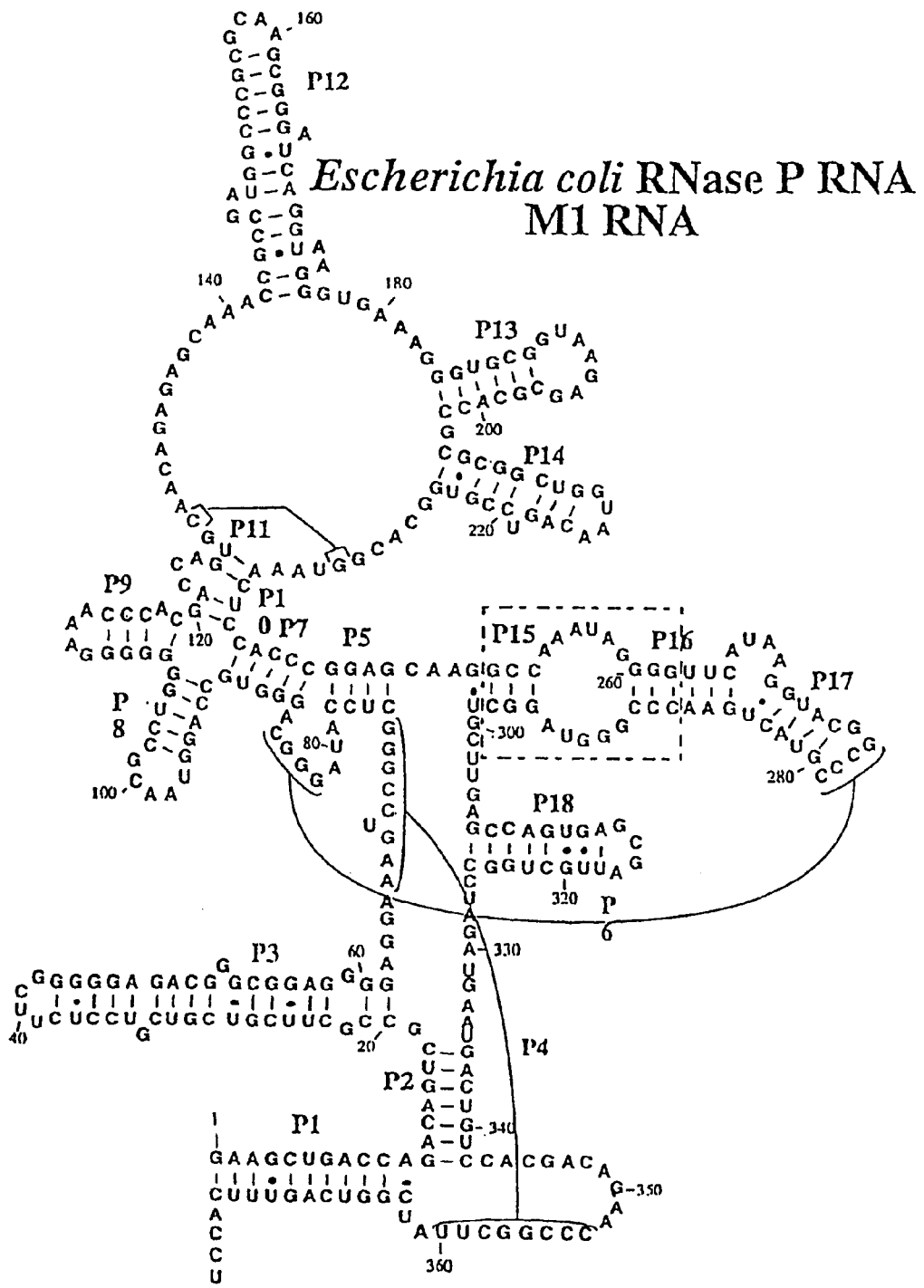
FIG. 1a shows the secondary structure of RNase P RNA derived from *Escherichia coli* (SEQ ID NO: 1)
Figure 1B:
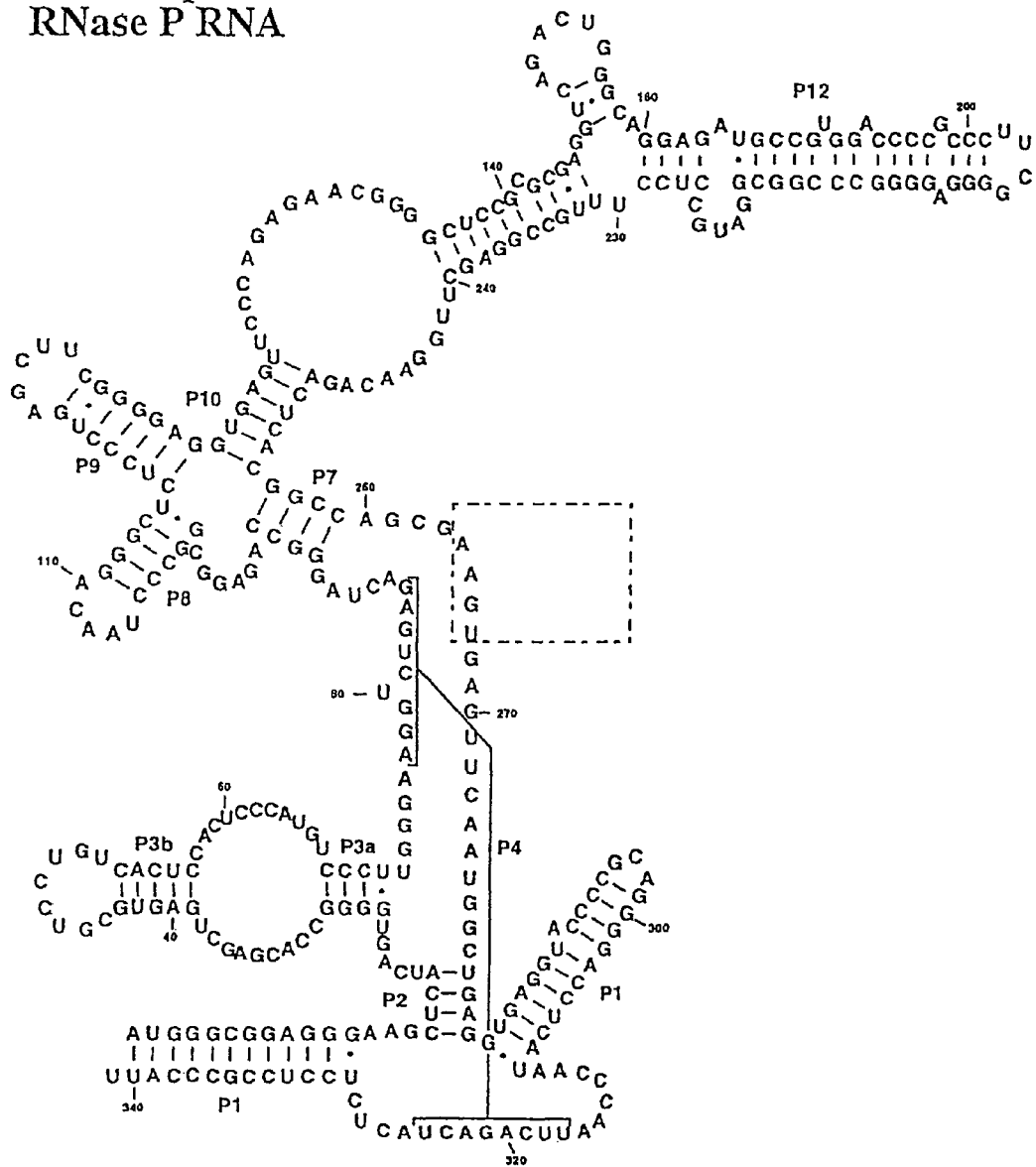
FIG. 1b shows the secondary structure of RNase P RNA derived from *Homo sapiens* (SEQ ID NO: 2). Residues marked in box correspond to residues constituting the P15 loop that is missing in *H. sapiens* RNase P RNA.

RNase P RNA is essential for the processing of tRNA precursors in bacteria as well as in eukaryotic (e.g. mammalian) cells (Altman and Kirsebom, 1999). Comparison of the secondary structures of RNase P RNA derived from bacteria with *Homo sapiens* RNase P RNA reveals significant structural differences (see FIG. 1 where *E. coli* and *H. sapiens* RNase P RNA are compared). The P15-loop is a functionally important domain of bacterial RNase P RNA, which is missing in *H. sapiens* RNase P RNA and in eukaryotic RNase P RNA in general (boxed in FIG. 1). The P15-loop of bacterial RNase P RNA interacts with the RNase P substrate through base-pairing, where the "GGU-motif" base pair with the RCCA (interacting residues underlined) located at the 3' end of the substrate (Altman and Kirsebom, 1999; Kirsebom and Virtanen, 2000). This is rationalized by the fact that most of the tRNA genes in bacteria encode the 3' CCA-motif while none of the tRNA in eukaryotes encode this sequence motif.

This example establishes a situation where a structural difference at the RNA level can be used to discriminate between a pathogen and its host. Thus, this fulfils the criteria that a chosen target RNA in the pathogen (here exemplified with the bacteria *E. coli*) should show structural differences compared to its counterpart in the host (in our example *H. sapiens*) in a region of the RNA that plays a functional important role.

Figure 2:
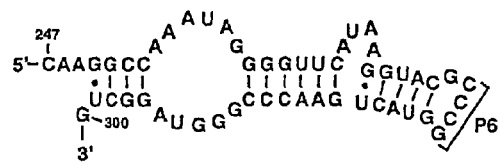
FIG. 2 shows examples of bacterial P15-loop variants (SEQ ID NOS: 3 and 5-9). At the bottom of the figure is an illustration of the secondary structure of the model 31-mer RNA representing the P15-loop derived from *Escherichia coli* RNase P RNA (SEQ ID NO: 4).
Figure 2:
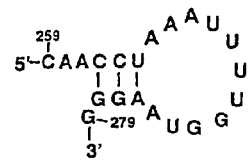
Figure 2:
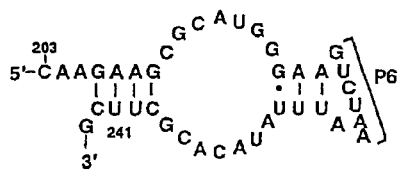
Figure 2:
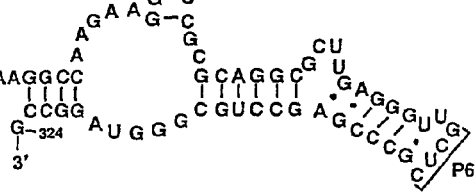
Figure 2:
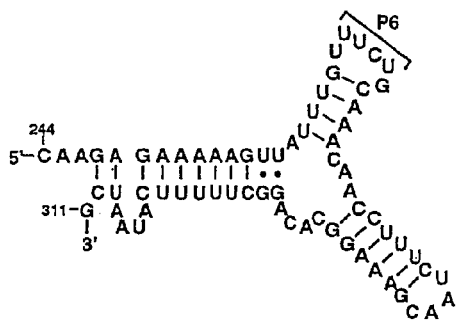
Figure 2:
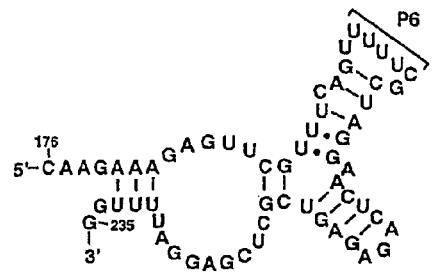
Figure 2:
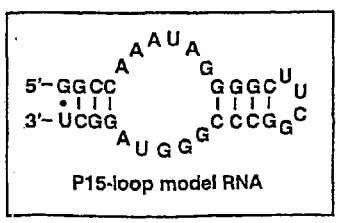

B Identification of Small Model by Representing Functional Important Domains The function of RNA is dictated by its structure. The overall structure of RNA molecules consists of small structural regions/domains that together build up the RNA structure. It is therefore possible to identify small stable RNA structural regions/domains that fold into the final structure when separated from the natural context in a large RNA molecule. Thus, small model RNA molecules representing functional important RNA regions/domains can be produced separately with retained conformation. This is clearly exemplified by the finding that the structure of the *E. coli* P15-loop is maintained when present in a small model 31-mer RNA (Kufel and Kirsebom, 1998). A library of several variants of P15-loop structures that have been identified in different bacteria together with the small model 31-mer RNA are depicted in FIG. 2.

This fulfils the criteria that it should be possible to produce a small model RNA harbouring a functionally important domain/region that does not change its structure when taken out of its natural context.

C Tools for Identification of "Metal Mimics"

Figure 3:
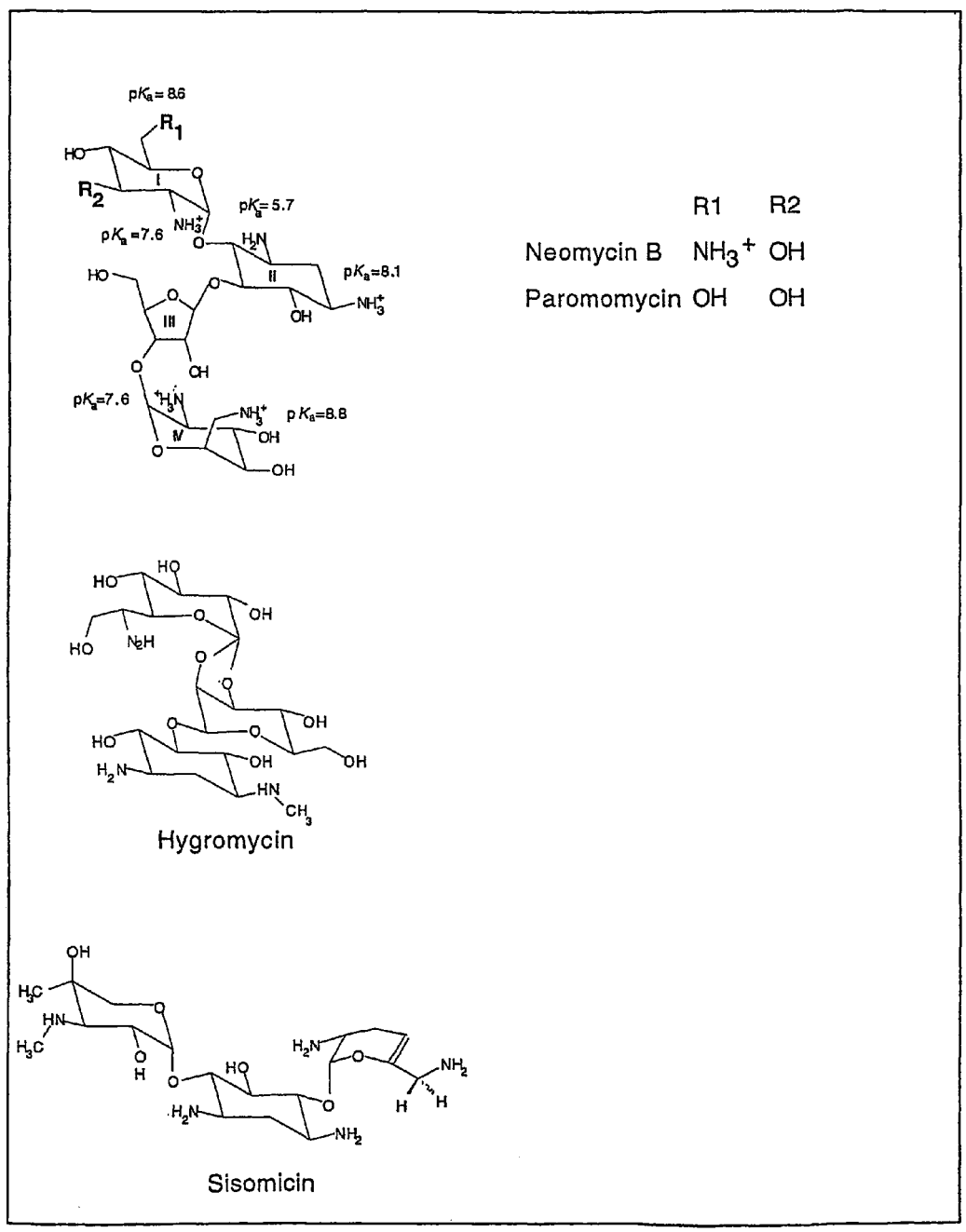
FIG. 3 shows example of aminoglycosides used in the present invention.

Bacterial RNase P RNA alone or in the presence of the protein subunit (referred to the C5 protein) cleaves its substrate in vitro correctly and efficiently and this cleavage activity can be inhibited by various aminoglycosides (Mikkelsen et al., 1999). The structure of some aminoglycosides that inhibit RNase P cleavage are depicted in FIG. 3. Aminoglycosides bind to RNA and displace functionally important divalent metal ions. Thus, aminoglycosides function as metal mimics (Mikkelsen et al., 2001).

Full-size *E. coli* RNase P RNA is cleaved at specific positions by Pb2+. Pb2+-induced cleavage of *E. coli* RNase P RNA is inhibited by the addition of for example the aminoglycoside neomycin B (Mikkelsen et al., 1999). The above discussed small model 31-mer RNA harbouring the *E. coli* P15-loop is also cleaved at specific positions in the presence of Pb2+(Kufel and Kirsebom, 1998). Surprisingly, Pb2+-induced cleavage of the 31-mer RNA is inhibited as a result of addition of various aminoglycosides as shown in Table 2. This clearly demonstrates that the small 31-mer model RNA comprising the functionally important P15-domain is a binding site for aminoglycosides.

TABLE 2

Summary of appKi values for inhibition of Pb2+-induced cleavage of the 31-mer RNA by various aminoglycosides. The P15-loop is derived from *Escherichia coli* RNase P RNA. appKi is defined as the aminoglycoside concentration that result in 50% inhibition of cleavage activity.

| Aminoglycoside | appKi (µM) 31-mer RNA | appKi (µM) inhibition of RNase P RNA cleavage |
|---|---|---|
| Neomycin B | 40 | 35 ± 12* |
| Paromomycin | 340 | 190 ± 12* |
| Sisomicin | 17 | — |
| 5-epi-Sisomicin | 1.2 | ≈3 |
| Hygromycin | 220 | — |

*The values are included for comparative reasons from Mikkelsen et al., 1999.

The observed appKi given in Table 2 are in the same concentration range as the range that inhibit RNase P cleavage activity. The appKi is defined as the aminoglycoside concentration that gives 50% inhibition of Pb2+-induced cleavage activity. A model RNA comprising the P15-loop (shown in FIG. 2) derived from *Mycobacterium tuberculosis* is also surprisingly cleaved at specific positions by Pb2+ and the Pb2+-induced cleavage of this particular model RNA is inhibited by several aminoglycosides some of which are shown in FIG. 3. This demonstrates that also model RNA molecules (comprising functionally important domains) built on naturally occurring sequences may be used.

The present inventors have now surprisingly found that Pb2+-induced cleavage can be used as a tool to identify small ligands that bind to a specific domain of a functionally important RNA. Note that all RNA molecules bind divalent metal ions, and binding of the divalent metal ion Pb2+ result in cleavage of the RNA given that it is positioned in a specific way (Brown et al. 1985). Therefore this approach is general and consequently any RNA molecule can be selected as a target. This fulfils the criteria to have a way to identify small ligands that bind to a small RNA molecule that represent a functionally important domain of an essential RNA molecule. The method relies on the idea that RNA cleavage is inhibited by small ligands. RNA cleavage can be performed by Pb2+ and a variety of other metal ions and enzymes. Other divalent metal ions such as Mg2+, Mn2+, Zn2+ etc can replace Pb2+, however, the advantage to use Pb2+ is that Pb2+-induced cleavage is much faster compared to cleavage by other divalent metal ions at physiological pH. Maintaining the pH at approximately 7 is to prefer since at high pH the structure of RNA changes and RNA is also degraded.

Detection of binding of a small ligand may also be achieved using various ribonucleases i.e. enzymes that cleave RNA at specific positions. For example RNase T1 cleaves preferentially 3' of single stranded guanosine residues. Thus, addition of a small ligand (i.e. inhibitor) may change the accessibility of single stranded guanosine residues and therefore binding of a small ligand would inhibit RNase T1 cleavage at the small ligand binding site.

The detection of binding of a small ligand to an RNA is not restricted to the detection of cleavage of RNA by various means. The detection of binding may also be by various spectroscopic or surface plasmon resonance methods. As examples of spectroscopic methods, binding of a small ligand may be detected for example as i) a shift of the spectra due to ligand binding, ii) as an increase or a decrease in stability of the RNA structure as a result of small ligand binding, which for example is measured as absorbance as function of temperature. Surface plasmon resonance may be used as follows. The model RNA comprising a functionally important region/domain is coupled to a surface using standard protocols. A solution containing potential inhibitors is passed over this surface and binding of an inhibitor (small ligand) is detected by reflection according to surface plasmon resonance technology.

When the aim is to screen for substances that bind to RNA using a mixture of different substances (for example a combinatorial library) a small model RNA molecule is linked to a solid surface and substances that bind to the RNA are identified using the tool of choice, for example Pb2+-induced cleavage or a specific ribonuclease or spectroscopic methods as discussed above.

Linkage of the RNA to a solid surface may be accomplished by biotionylating the 5' or 3' end of the RNA. The so obtained RNA is subsequently allowed to bind to streptavidine beads or streptavidine coated tubes. Alternatively, a model RNA (comprising a functionally important region/domain) carrying a 5' or 3' single stranded region is allowed to hybridise to a oligonucleotide that is anchored to a solid support. Here the 5' or 3' is complementary to the oligonucleotide that is anchored to the solid support.

D Suppression of Toxic Side-Effects and Appearance of Resistance

When a specific inhibitor of a targeted RNA, using a small model RNA representing a functionally important domain of an RNA present in given pathogen, has been identified the inhibitor may be tested for inhibitory action using the larger RNA as the target and an appropriate assay system. In the above discussed exemplification a novel small compound that binds the P15-loop derived from e.g. *M. tuberculosis* is tested for inhibitory activity of the full-size *M. tuberculosis* RNase P RNA both alone and in the presence of the RNase P protein C5. It is essential to establish that the inhibitor inhibits RNase P RNA cleavage in the presence of C5, since C5 is essential for activity in vivo. A crucial criteria is that the inhibitor inhibits the activity of the targeted RNA with high specificity. This means, in this example that the inhibitor should inhibit *M. tuberculosis* RNase P with high specificity and should not inhibit human RNase P activity. Thus, inhibition studies using human RNase P are performed to ensure that the inhibitor does not inhibits its activity.

Moreover, the method can be used to investigate and identify inhibitors that are highly specific or less specific. This is achieved by using, for example, RNase P derived from different bacterial sources and study their catalytic performance in the presence of the chosen inhibitor. If an inhibitor with high specificity is to be identified, then the inhibitor should (in the given example *M. tuberculosis* RNase P) not inhibit the activity of *E. coli* and other bacterial RNase P variants. The main advantages with this are: i) Growth of "house-keeping" bacteria is not inhibited in the presence of the inhibitor which as a consequence will suppress unwanted side-effects and ii) possible suppression of the appearance of resistance against the inhibitor that propagate via horizontal gene-transfer. If an inhibitor with broad spectrum, such as a broad spectrum antibiotic, is to be identified then the method can be used to identify inhibitors that inhibit a large number of different bacteria spp. or classes of bacteria.

Many antibiotics that are used today cause severe side-effects. Additionally, as of today a necessary, time-consuming, important and expensive step in drug development is the usage of experimental animal systems in the process to identify novel drugs with low levels of toxic side-effects.

The mechanisms behind toxicity and severe side-effects are not understood and several potential causes have been discussed in the literature. The finding by the present inventors that aminoglycosides inhibit Klenow pol and PARN suggest that inhibition of nucleic acid metabolising enzymes may be a common mechanism by which aminoglycosides cause unwanted side effects. In support of this we have shown that several other nucleic acid metabolising enzymes, among them Bam HI restriction enzyme, HIV reverse transcriptase, bacterial RNase H, mammalian poly(A) polymerase, Taq DNA polymerase and T7 RNA polymerase, can be inhibited in vitro by the addition of 0.1-5 mM neomycin B. This shows that binding to and inhibition of metalloenzymes involved in breaking and forming phosphodiesterbonds is a general feature of aminoglycosides.

A significant advantage of the invention is that it can be used to test the inhibitors that bind the target RNA for binding to proteins that play crucial roles during gene expression. The reasons fox this are: i) We screen for inhibitors that bind to pockets on RNA that bind divalent metal ions that are important for function. ii) Many protein enzymes also bind divalent metal ions that are important for function. iii) Therefore, inhibitors that bind to RNA and displace divalent metal ions also have the potential to bind to protein enzymes and thereby displace divalent metal ions that are crucial for the function of such proteins. The present inventors have demonstrated that several metallo-enzymes are inhibited by the addition of various aminoglycosides. Thus, a small ligand can have the potential to bind to both RNA and protein enzymes and inactivate their function by displacing functionally important divalent metal ions. This may cause severe toxic side effects. To circumvent the problem of inhibitor-binding to essential metallo-enzymes of the host the criteria is that the inhibitors that are identified to bind to RNA should not interact/bind to protein enzymes that depend on divalent metal ions for activity. The invention therefore makes a "counter screening" step possible, where the inhibition of a set of specific house keeping protein enzymes is tested. Thus, this step has the potential to identify toxic side effects at an early stage in drug development and thereby reduce time and usage of experimental animal systems.

E Further Steps in the Process of Drug Development

After the outlined in vitro screening for novel RNA binding compounds, inhibition studies and "counter screening" investigations, the identified inhibitors may be passed through series of in vivo inhibition studies in bacterial cultures and cell cultures. Here the objective is to further establish the identified inhibitor(s) as (a) potential lead compound(s) for drug development.

Materials and Methods

RNA Preparation, RNase P and Pb2+-Induced Cleavage

Preparation of Model RNA.

The different gene constructs were put behind the T7 promoter and the RNA was generated using T7 DNA dependent RNA polymerase (or its equivalent) according to standard protocols. Shorter RNA molecules can be synthesized chemically however, here the size of the RNA is of crucial importance i.e. the RNA cannot be too large. When necessary the RNA was labelled internally, at the 5' or 3' end with $^{32}$P Alternatively, the RNA can be labelled by other means-using $^{3}$H or $^{14}$C or for example fluorescence labelling.

RNase P Cleavage and Pb2+-Induced Cleavage.

RNase P cleavage and Pb2+-induced cleavage was performed and monitored according to standard protocols as described by Kufel and Kirsebom (1998). To determine the appKi value for a given substance RNase P cleavage or Pb2+-induced cleavage conditions were adjusted in such a way that measurements were carried out in the linear portion of the curve of kinetics of the cleavage reaction. Cleavage efficiency was plotted as a function of the concentration of the compound X under study, and appKi is defined as the concentration resulting in 50% inhibition of cleavage activity.

Protein Related Methods Essential for Counter-Screening

Several enzymes depending on metal ions for activity are particularly relevant for this invention. Many of these enzymes are essential for cell survival, for example the so called house-keeping enzymes. Examples of such enzymes are: mammalian poly(A) polymerase (PAP), mammalian poly(A)-specific ribonuclease (PARN) and E. coli Klenow DNA polymerase (POL I), phospholipase C, Rnase H, T7 DNA dependent polymerase, RNA polymerase, Taq polymerse, BamH1 and reverse transcriptase.

Assay and Quantitation of Klenow and PARN Activities.

To test for Klenow polymerase activity we used the Klenow (D355A, E357A) recombinant polypeptide, in which the 3'-5' exonuclease active site was inactivated by site directed mutagenesis, as the enzyme and a double stranded DNA fragment, generated by hybridisation of oligonucleotides 5'-TCGCAGCCGTGAG-3' (SEQ ID NO: 10) and 5'-ATC-CAAGCTCACGGCTGCGA-3' (SEQ ID NO: 11), as the template. The DNA template was prepared as described (Eger and Benkovic 1992). The reactions were performed in 10 microliter in the present of 100 mM HEPES-KOH pH 7.0, 1 mM DTT, 0.5 microgram/microliter BSA, 150 mM KCl, 4 mM MgCl$_2$, 10 mM spermidine, 1 micromolar DNA template, 0.3 micromolar (alpha-$^{32}$P) dCTP (3000 Ci/mmol) (Amersham Pharmacia Biotech) and contained 0.2-1 nM of indicated Klenow pol fragment. Reactions were incubated at 30° C. for 5-20 minutes and then stopped by the addition of 10 microliter loading buffer (80% formamide (v/v), 0.1% xylene cyanol, 0.1% bromophenol blue, 50 mM Tris-HCl pH 7.9, 50 mM EDTA). The reacted DNA was fractionated by 10% polyacrylamide (19:1 acrylamide/bisacrylamide 30:0.8)-7 M urea gel electrophoresis. The obtained gel was scanned using a 400 S PhosphorImager (Molecular Dynamics). When dCTP was titrated, the DNA template concentration was 1 micromolar, while the dCTP concentration was 50 micromolar when the DNA template was titrated. The pH of the reactions were 7.0 if not stated otherwise. The consumption of substrate (dCTP or DNA) was controlled so that not more than 20% of its total amount was consumed.

Homogeneously purified calf thymus PARN 54 kDa active fragment was used as the source of PARN (Martinez et al. 2000). Recombinant full length human PARN was expressed and purified as described (Martinez et al. 2000). As the substrate we used L3(A$_{30}$) RNA radioactively labelled in its poly(Å) tail (Åström et al. 1991). Assay conditions and 1-D TLC quantitation procedures were as previously described (Åström et al. 1992). The pH of the deadenylation reactions were 7.0, unless stated otherwise. The consumption of L3(A$_{30}$) RNA substrate was controlled so that no more than 20% of it was consumed.

The aminoglycosides were purchased from Sigma Chemical Co. and added amount was as indicated. The polymerisation or deadenylation efficiencies were plotted as a function of the concentration of the aminoglycoside under study. The $_{app}K_i$ was defined as the concentration of added aminoglycoside resulting in 50% inhibition of Klenow pol or PARN activities, respectively. $K_i$ values were obtained by plotting the determined $-(K_M/V_{max})$ values against the concentration of aminoglycoside under study.

Fe(II) Mediated Hydroxyl Radical Cleavage of Proteins.

2-4 microgram of purified recombinant Klenow pol fragment or mutant thereof, dialysed against buffer F (20 mM HEPES-KOH pH 7.0, 5 mM NaCl) on a Milipore "V" Series Membrane (Millipore) for 30 minutes at 4° C., was incubated for 30 minutes at 37° C. in 50 mM HEPES pH 7.0, 5 mM NaCl, 20 micromolar Fe(NH$_4$)$_2$SO$_4$ and 10 mM DTT in total volume of 10 microliter. The incubations were stopped by the addition of 10 microliter of 2×SDS-loading buffer (100 mM Tris-HCl pH 6.8, 2% (w/v) SDS, 200 mM DTT, 16%(v/v) glycerol, 0.05%(w/v) bromolphenol blue and 50 mM EDTA). The amount of added Mg(II)-ions, Mn(II)-ions or aminoglycoside was as indicated. Reacted polypeptides were fractionated by 10% SDS-polyacrylamide gel electrophoresis and subsequently visualised by silver staining.

Recombinant PARN polypeptides expressed in E. coli were purified and radioactively labelled in their N-termini. Fe(II) mediated hydroxyl radical cleavage, of PARN was essentially performed as described above. Reacted samples were subjected to 10% SDS-polyacrylamide gel electrophoresis and the resulting gel was subsequently visualized and quantified using a 400 S PhosphorImager (Molecular Dynamics). In the Mg(II) and Mn(II) ions competition experiments, MgCl$_2$ or MnCl$_2$ was added at indicated concentration in the presence of 20 micromolar Fe(NH$_4$)$_2$SO$_4$.

In Vivo Method

The objective with this embodiment of the novel method according to the invention is two-fold: i) to identify novel inhibitors that interact/bind with/to functionally important domains of selected RNA targets that are essential for growth of microorganisms including virus under in vivo conditions and ii) to test novel inhibitors that have been identified using the in vitro strategy described above for binding to its selected target under in vivo conditions. The RNA targets are selected based on the same criteria as described under paragraphs A through C.

Step 1

Figure 4:
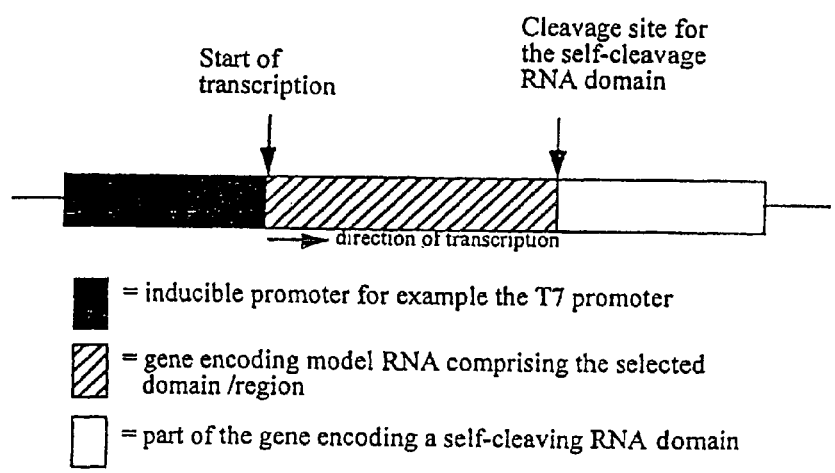
FIG. 4 shows a gene construct encoding model RNA and a self-cleaving RNA element.

Generate a gene encoding the selected RNA domain behind an inducible promoter (see FIG. 4). This gene construct is either synthesized chemically or generated by PCR technology (polymerase chain reaction) with suitable oligodeoxynucleotide primers that are complementary to specific regions on the gene that encodes the model RNA comprising the selected RNA domain/region.

In addition, this gene construct carries a self-cleaving RNA structure element downstream of the gene construct encoding the RNA target. The transcription product carries the selected RNA domain plus a self-cleaving RNA structural element. After self-cleavage the cleaved transcript consists of only the selected model RNA comprising the selected domain/region with a 2';3'-cyclic phosphate at the 3' end. The advantage to have the 2';3'-cyclic phosphate at the 3' end is that it blocks the action of 3' exoribonucleases and thereby degradation of the selected RNA domain inside for example a bacteria. In addition, the presence of the self-cleaving RNA ensures that a desired size/length of the selected RNA target is produced.

Step 2

The so obtained gene construct is subsequently introduced into a suitable plasmid vector.

Step 3

Following the outline described above a vector harboring the gene construct according to step 1 is transformed into suitable bacterial strains and expressed by induction of the inducible promoter. Below are two examples of how the bacterial strains can be used in the context of the invention.

Example 1

Test of In vitro Identified Inhibitors

Two bacterial strains are used. In one of the strains the selected RNA will be expressed (bottom case in FIG. 5). Due to the presence of high intracellular concentration of the selected RNA (model RNA used comprising the selected RNA domain/region to identify the inhibitor according to the outline described above) the inhibitor will bind mainly to the selected RNA. The essential full-size RNA comprising the selected RNA will not bind the inhibitor since the selected RNA domain is in large excess over the essential full-size RNA. The result is that the strain will grow. In the other strain the selected RNA is not produced as a result of repression of its gene or due to fact that the plasmid is missing or that it does not encode the selected RNA (as indicated top of FIG. 5, example with plasmid not encoding RNA gene). Addition of inhibitor will therefore result in inhibition of growth since the inhibitor will bind to the selected RNA region/domain on the full-size RNA, which as a consequence result in inhibition of the activity of the RNA. In conclusion, this protocol identifies inhibitors also functioning under in vivo conditions. Inhibitors that allow both strains to grow are of no interest.

Example 2

Selection of Novel Inhibitors

The above outline can also be used to select for inhibitors that bind/interact with a selected domain/region directly. Here again two strains are used one in which the selected model RNA comprising the RNA domain/region is expressed (strain A bottom FIG. 5) and one in which the selected model RNA comprising the RNA domain/region is not expressed (strain B top FIG. 5). Here the criteria are that addition of an inhibitor or pool thereof (for example combinatorial libraries) of potential inhibitors should allow growth in strain A but not in strain B (FIG. 5) demonstrating that growth depends on the presence of high intracellular concentration of the model RNA comprising the selected RNA domain/region. One achievement using this set-up is that it allows for the identification of inhibitors that penetrate a bacteria/cell and bind/interact with the selected RNA domain/region under in vivo conditions.

Figure 5:
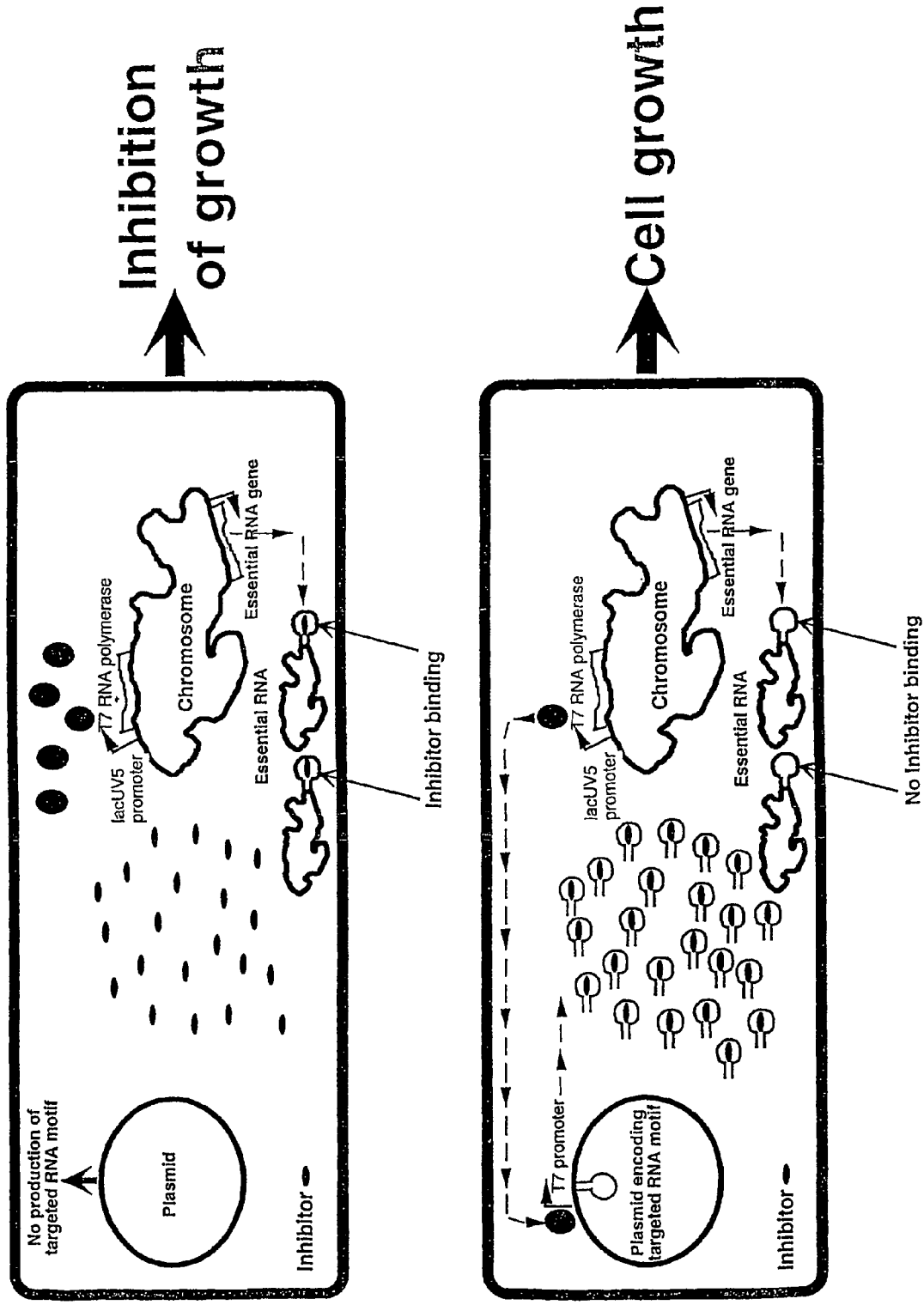
FIG. 5 is schematic view illustrating a summary of the in vivo approach described below.

In the example illustrated in the top of FIG. 5 the addition of an inhibitor (indicated in black ellipsis) results in inhibition of growth. The reason for growth inhibition is that the inhibitor binds (thin arrows) to a domain of an essential RNA thereby inactivates its function. In the bottom of FIG. 5, a plasmid carrying a gene encoding the model RNA comprising the selected RNA domain/region (which is taken from the essential RNA molecule indicated in the figure) behind an inducible promoter (here T7 promoter) is introduced. The outcome is that high intracellular concentration of the targeted RNA motif is, obtained indicated by the small "hairpins". These small RNA molecules bind the inhibitor and the result is sustained growth of the cell since the binding of the inhibitor to the essential RNA molecule is out competed.

CONCLUDING REMARK

The above outlined exemplification of the method according to the invention is not restricted to the given examples but can be applied to any pathogen that harbours an essential RNA molecule with a unique metal binding domain that is absent or show structural differences in comparison with its host analogue.

The metal mimic concept is that an inhibitor binds to an RNA or protein and thereby displaces a divalent metal ion(s) important for function. The metal mimic concept together with the outlined method can therefore be used to identify any ligand that displaces functionally important divalent metal ions in any macromolecule, i.e. RNA or protein. Thus, the method of the invention can be used to identify inhibitors that bind to any specific RNA molecules or proteins that are essential for cell growth, proliferation and differentiation. Consequently, the method can be used to identify inhibitors that suppress the growth of a tumor cell. Similarly, the method can be used to identify antiviral inhibitors.

REFERENCES

Altman, S. & Kirsebom, L. A. (1999) in The RNA World, eds. Gesteland, R. F., Cech, T. R. &
Atkins, J. F. (Cold Spring Harbor Lab. Press, Plainview, N.Y.), pp. 351-380.
Åström, J. et al. (1991). *EMBO J.* 10, 3067-3071.
Åström, J. et al. (1992). *J. Biol. Chem.* 267, 18154-18159.
Brown, R. S., Dewan, J. C. & Klug, A. (1985) Biochemistry 24, 4785-4801.
Eger, B. T. and S. J. Benkovic (1992). *Biochemistry* 31, 9227-9236.
Guerrier-Takada, C., Gardiner, K., Marsh, T., Pace, N. & Altman, S. (1983) *Cell* 35, 849-857.
Hermann, T. & Westhof, E. (1998) *J. Mol. Biol.* 276, 903-912.
Kirsebom, L. A. & Svärd, S. G. (1994) *EMBO J.* 13, 4870-4876.
Kirsebom, L. A. & Virtanen, A. (2001). In "Inhibition of RNase P processing". (Eds Schroeder and Wallis). RG Landes Co. pp 56-72.
Kufel, J. & Kirsebom, L. A. (1998) *RNA* 4, 777-788.

MacBeath, G. and S. L. Schreiber (2000). *Science* 289, 1760-1763.

Martinez, J. et al. (2000). *J Biol Chem* 275, 24222-24230.

Mikkelsen, N. E., Brännvall, M., Virtanen, A. & Kirsebom, L. A. (1999) *Proc. Natl. Acad. Sci. USA* 96, 6155-6160.

Mikkelsen, N. E., Johansson, K., Virtanen, A. & Kirsebom, L. A. (2001) Nature Struc. Biol. 8, 510-514.

Steitz, T. A. (1999) *J. Biol. Chem.* 274, 17395-17398.

Steitz, T. & Steitz, J. A. (1993) *Proc. Natl. Acad. Sci. USA* 90, 6498-65.02.

Svärd, S. G., Kagardt, U. & Kirsebom, L. A. (1996) *RNA* 2, 463-472.

Walter, F., Vicens, Q. & Westhof, E. (1999) *Curr. Opin. Chem. Biol.* 3, 694-704.

Warnecke, J. M., Fürste, J. P., Hardt, W.-D., Erdmann, V. & Hartmann, R. K. (1996) *Proc. Natl. Acad. Sci. USA* 93, 8924-8928.

The invention claimed is:

1. A method for detection of a novel pathogen inhibitor, comprising the following steps:
   a) providing a small RNA molecule comprising at least one functionally important, pathogen unique and divalent metal ion binding region/domain of an essential RNA macromolecule of a pathogen of bacterial origin, wherein the divalent metal ion binding region/domain of the RNA macromolecule is essential for growth, proliferation and/or differentiation of the pathogen, wherein the small RNA molecule is P15, P15/P16-loop, P16 or P17 of RNase P RNA of bacterial origin;
   b) in vitro screening for a compound which displaces divalent metal ions that interact/bind to said small RNA molecule and identifying a compound interacting/binding to said small RNA molecule as a potential inhibitor;
   c) in vitro testing a potential inhibitor compound interacting/binding to said small RNA molecule for inhibition of human metal ion dependent enzyme, and selecting the compound as a potential pathogen inhibitor if it does not inhibit said enzyme;
   d) testing the potential pathogen inhibitor compound for inhibition of a corresponding full size RNA molecule originating from the pathogen, both alone and in the presence of an interacting cell protein if necessary for function; and
   e) if the potential pathogen inhibitor compound inhibits the corresponding full size RNA molecule originating from the pathogen, cultivating the corresponding pathogen in the presence of the potential pathogen inhibitor compound, wherein inhibition of the pathogen identifies the compound as a pathogen inhibitor.

2. A method according to claim 1, wherein the small RNA molecule provided in a) is linked to a solid support.

3. A method according to claim 1, wherein the in vitro screening step (b) is by detection of RNA or protein cleavage in vitro, wherein interaction/binding of an inhibiting compound prevents RNA/protein cleavage.

4. A method according to claim 3, wherein the RNA/protein cleavage is induced by $Pb^{2+}$.

5. A method according to claim 3 wherein the in vitro screening step (b) is by detection of a spectroscopic shift due to an interacting/binding compound.

6. A method for detection of a novel pathogen inhibitor, comprising the following steps:
   a) providing a small RNA molecule comprising at least one functionally important, pathogen unique and divalent metal ion binding region/domain of an essential RNA macromolecule, wherein the small RNA molecule is provided in a vector carrying gene sequences encoding the small RNA molecule harbouring sequences encoding functionally important regions/domains of essential RNA molecules which are autonomous divalent metal ion binding sites for recombinant production of the small RNA molecule, wherein the gene sequences encode P15, P15/P16-loop, P16 or P17 of RNase P RNA of bacterial origin;
   b) in vitro screening for a compound which displaces divalent metal ions that interact/bind to said small RNA molecule, wherein the in vitro screening is by detection of RNA or protein cleavage in vitro and wherein interaction/binding of an inhibiting compound prevents RNA/protein cleavage, and identifying a compound interacting/binding to said small RNA molecule as a potential inhibitor;
   c) in vitro testing a potential inhibitor compound interacting/binding to said small RNA molecule for inhibition of human metal ion dependent enzyme, and selecting the compound as a potential pathogen inhibitor if it does not inhibit said enzyme;
   d) testing the potential pathogen inhibitor compound for inhibition of a corresponding full size RNA molecule originating from the pathogen, both alone and in the presence of an interacting cell protein if necessary for function; and
   e) if the potential pathogen inhibitor compound inhibits the corresponding full size RNA molecule, cultivating the corresponding pathogen in the presence of the potential pathogen inhibitor compound, wherein inhibition of the pathogen identifies the compound as a pathogen inhibitor.

7. A method according to claim 1, wherein the human metal dependent enzyme comprises a nucleic acid-metabolizing enzyme.

8. A method according to claim 6, wherein the human metal dependent enzyme comprises a nucleic acid-metabolizing enzyme.

9. A method according to claim 1, wherein the bacterial origin is *Mycobacterium tuberculosis*.

10. A method according to claim 1, wherein the compound is an aminoglycoside.

11. A method according to claim 6, wherein the compound is an aminoglycoside.

12. A method according to claim 1, wherein the human metal dependent enzyme is one or more of mammalian poly(A) polymerase (PAP), mammalian poly(A)-specific ribonuclease (PARN), *E. coli* Klenow DNA polymerase (POL I), phospholipase C, RNase H, T7 DNA dependent polymerase, RNA polymerase, Taq polymerase, BamH1, and reverse transcriptase.

13. A method according to claim 6, wherein the human metal dependent enzyme is one or more of mammalian poly(A) polymerase (PAP), mammalian poly(A)-specific ribonuclease (PARN), *E. coli* Klenow DNA polymerase (POL I), phospholipase C, RNase H, T7 DNA dependent polymerase, RNA polymerase, Taq polymerase, BamH1, and reverse transcriptase.

* * * * *

SEQUENCE LISTING

<160> NUMBER OF SEQ ID NOS: 11

<210> SEQ ID NO 1
<211> LENGTH: 368
<212> TYPE: RNA
<213> ORGANISM: Escherichia coli

<400> SEQUENCE: 1
gaagcugacc agacagucgc cgcuucgucg ucuccucuuc gggggagacg gcggagggga    60
ggaaagccgg gcuccauagg gcagggugcc agguaacgcc uggggggggaa acccacgacc   120 agugcaacag agagcaaacc gccuggcccg cgcaagcggg ucaggugggu gaaagggugc   180
gguaagagcg caccgcgcgg cugguaacag ccguggcacg guaaacucca cccggagcaa   240
ggccaaauag ggguucauaa gguacggccc guacugaacc cggguaggcu gcuugagcca   300
gugagcgauu gcuggccuag augaaugacu guccacgaca gaacccggcu uaucggucag   360
uuucaccu                                                           368

<210> SEQ ID NO 2
<211> LENGTH: 341
<212> TYPE: RNA
<213> ORGANISM: Homo sapiens

<400> SEQUENCE: 2
aaugggcgga gggaagcuca ucagugggggc cacgagcuga gugcguccug ucacuccacu    60
cccaugaccc uugggaaggu cugagacuag ggccagaggc ggcccuaaca gggcucuccc   120
ugagcuucgg ggaggugagu ucccagagaa cggggcuccg cgcgagguca gacugggcag   180
gagaugccgu ggaccccgcc cuucggggag gggcccggcg gaugccuccu uugccggagc   240
uuggaacaga cucacggcca gcgaagugag uucaauggcu gaggugaggu accccgcagg   300
ggaccucaua acccaauuca gacuacucuc cuccgcccau u                       341

<210> SEQ ID NO 3
<211> LENGTH: 78
<212> TYPE: RNA
<213> ORGANISM: Mycobacterium tuberculosis

<400> SEQUENCE: 3
caaggccaag aaggccgcac cgaaagugcg gccgcgcagg cgcuugaggg uugcucgccc    60
gagccugcgg guaggccg                                                 78

<210> SEQ ID NO 4
<211> LENGTH: 31
<212> TYPE: RNA
<213> ORGANISM: artificial sequence
<220> FEATURE:
<223> OTHER INFORMATION: P15-loop model RNA

<400> SEQUENCE: 4

-continued

```
ggccaaauag gggcuucggc ccggguaggc u                              31

<210> SEQ ID NO 5
<211> LENGTH: 54
<212> TYPE: RNA
<213> ORGANISM: Escherichia coli

<400> SEQUENCE: 5
caaggccaaa uagggguuca uaagguacgc ccgguacuga acccgggguag gucg    54

<210> SEQ ID NO 6
<211> LENGTH: 39
<212> TYPE: RNA
<213> ORGANISM: Helicobacter pylori

<400> SEQUENCE: 6
caagaagcgc augggaaguc uaaauuuaua cacgcuucg                      39

<210> SEQ ID NO 7
<211> LENGTH: 68
<212> TYPE: RNA
<213> ORGANISM: Chlamydia trachomatis

<400> SEQUENCE: 7
ccagagaaaa aguuauuugu uucugcaaac aaccuuucua acgaaaggca caggcuuuuu   60
cauaaucg                                                        68

<210> SEQ ID NO 8
<211> LENGTH: 21
<212> TYPE: RNA
<213> ORGANISM: Mycoplasma hypneumoniae

<400> SEQUENCE: 8
ccaccuaaau uuugguaagg g                                         21

<210> SEQ ID NO 9
<211> LENGTH: 60
<212> TYPE: RNA
<213> ORGANISM: Simkania negevensis

<400> SEQUENCE: 9
caagaaagag uucguuucag uuuuucgcua ggaacucaga gagucgcucg aggauuuugg   60

<210> SEQ ID NO 10
<211> LENGTH: 13
<212> TYPE: DNA
<213> ORGANISM: artificial
<220> FEATURE:
<223> OTHER INFORMATION: DNA template oligonucleotide

<400> SEQUENCE: 10
tcgcagccgt gag                                                  13

<210> SEQ ID NO 11
<211> LENGTH: 20
<212> TYPE: DNA
<213> ORGANISM: artificial
<220> FEATURE:
<223> OTHER INFORMATION: DNA template oligonucleotide

<400> SEQUENCE: 11
atccaagctc acggctgcga                                           20
```